US008440590B2

(12) United States Patent
Oostendorp et al.

(10) Patent No.: US 8,440,590 B2
(45) Date of Patent: May 14, 2013

(54) METHOD FOR CONTROLLING SOYBEAN RUST

(75) Inventors: Michael Oostendorp, Basel (CH); Franz Brandl, Basel (CH); Sergio Paiva, Sao Paulo (BR); Nestor Gabriel Da Silva, Sao Paulo (BR); Ronald Zeun, Stein (CH); Ulrich Johannes Haas, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 322 days.

(21) Appl. No.: 12/446,815

(22) PCT Filed: Oct. 23, 2007

(86) PCT No.: PCT/EP2007/009178
§ 371 (c)(1),
(2), (4) Date: Jun. 1, 2011

(87) PCT Pub. No.: WO2008/049575
PCT Pub. Date: May 2, 2008

(65) Prior Publication Data

US 2011/0312493 A1 Dec. 22, 2011

(30) Foreign Application Priority Data

Oct. 26, 2006 (EP) .................................... 06022366

(51) Int. Cl.
*A01N 25/26* (2006.01)
*A01N 57/00* (2006.01)
*A01N 57/18* (2006.01)

(52) U.S. Cl.
USPC ............................ 504/100; 504/127; 504/128

(58) Field of Classification Search ....................... None
See application file for complete search history.

(56) References Cited

U.S. PATENT DOCUMENTS

2009/0023687 A1 * 1/2009 Haas ............................ 514/114

FOREIGN PATENT DOCUMENTS

| | | |
|---|---|---|
| DE | 10137781 | * 9/2002 |
| EP | 1606999 | 12/2005 |
| WO | 2005041669 | 5/2005 |
| WO | 2005122771 | 12/2005 |
| WO | 2006037633 | 4/2006 |
| WO | 2006066810 | 6/2006 |
| WO | 2006128095 | 11/2006 |
| WO | 2006131230 | 12/2006 |
| WO | 2007017256 | 2/2007 |
| WO | 2007054835 | 5/2007 |
| WO | 2007068421 | 6/2007 |
| WO | 2007128541 | 11/2007 |
| WO | 2008135480 | 11/2008 |
| WO | 2008148476 | 12/2008 |

OTHER PUBLICATIONS

"Method for protecting useful plants or plant propagation material" Research Disclosure, Mason Publications, Hampshire, GB, vol. 507, No. 2, Jul. 1, 2006, p. 783, XP002442483, ISSN: 0374-4353.

* cited by examiner

*Primary Examiner* — Alton Pryor
(74) *Attorney, Agent, or Firm* — Brian D. McAlhaney

(57) ABSTRACT

A method for controlling asian soybean rust comprising (α) applying a pesticidal composition (A) to a glyphosate tolerant soybean plant propagation material, and (β) applying a pesticidal composition (B) to the resulting soybean plant, part of plant and/or the locus thereof one or more times: i) before emergence, ii) after emergence, or iii) both (i) and (ii), provided that composition (A) comprises one or more of flutriafol, triticonazole, tebuconazole, ipconazole, epoxyconazole, orysastrobin, prothioconazole fluoxastrobin, azoxystrobin, furametpyr, cyproconazole, a compound of formula (I) and a compound of formula (B), and pesticide composition (B) comprises glyphosate; wherein compound (I) is represented by or a tautomer of such a compound, and compound (B) is represented by formula or a tautomer of such a compound.

(I)

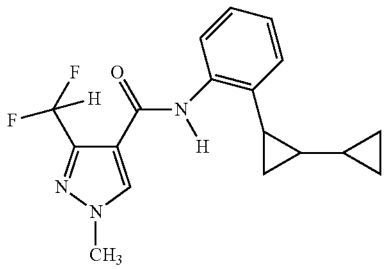

(B)

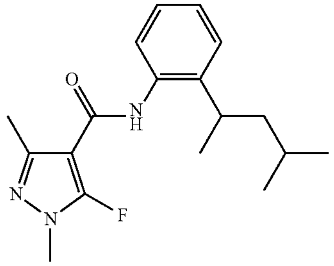

4 Claims, No Drawings

METHOD FOR CONTROLLING SOYBEAN RUST

This application is a 371 of International Application No. PCT/EP2007/009178 filed Oct. 23, 2007, which claims priority to EP 06022366.6, filed Oct. 26, 2006, the contents of which are incorporated herein by reference.

The present invention relates to methods for controlling asian soybean rust, in particular on glyphosate tolerant soybeans, and plant propagation material thereof treated with certain fungicides.

The development of herbicide tolerant crops allows for the greater use of post-emergent herbicides during agricultural cultivation of the crop. One example of a post-emergent herbicide is N-phosphonomethylglycine, also known as glyphosate, a well known herbicide that has activity on a broad spectrum of plant species. Glyphosate is the active ingredient of Roundup® (Monsanto Co.) and Touchdown® (Syngenta Crop Protection. Inc), a safe herbicide having a desirably short half-life in the environment. When applied onto a plant surface, glyphosate moves systemically through the plant. Glyphosate is toxic to plants by inhibiting an enzyme in the shikimic acid pathway that provides a precursor for the synthesis of aromatic amino acids. Plants, fungi and some bacteria contain the 5-enolpyruvylshikimate-3-phosphate synthase (EPSPS) enzyme that is sensitive to the toxic effects of glyphosate Asian soybean rust (ASR) can be caused by either of two fungal species, *Phakopsora pachyrhizi* or *P. meibomiae. P. meibomiae* has not been detected in the continental U.S., and is not known to be of economic importance to crop production. However, *P. pachyrhizi*, a species endemic to Asia, is a devastating disease. In untreated fields in Asia and South America, yield losses ranging from 10 to 80% have been reported due to premature defoliation, fewer seeds, lighter seeds and poor seed quality.

*P. pachyrhizi* is now present in most of the soybean growing areas of the world, it originated in NE Asia and was first reported on soybean in Africa in 1997. The first detection in the Americas was in Paraguay in 2001, and from there it spread rapidly to all soybean-growing areas of Brazil. It was first recorded in the northern hemisphere in 2004 in Colombia. Hurricane Ivan in September of 2004 was most likely responsible for the recent introduction into the U.S.

ASR is carried long distances by wind currents; however, field-to-field transmission through contaminated clothing is also common. The fungus is not seed-transmitted. Most of the knowledge about ASR was developed in subtropical and tropical areas of the world. As with any new disease, its epidemiology and resulting control strategies might change in the temperate growing areas of the U.S.

In addition to soybeans, the Asian soybean rust fungus is able to infect over 30 legumes such as lima and butter beans, green beans, kidney beans, cowpeas, pigeon peas, yam bean and jicama. Kudzu is also a suitable host.

To date for 2006, there are 28 counties in six states within the United States with soybean rust. In comparison to 2005, there were 21 counties with soybean rust in early August.

Currently, fungicides are the only effective option available for management of soybean rust. Soybean rust-resistant cultivars are not available and cultural practices like row width, planting date, and tillage may have minimal or inconsistent effects on soybean rust development.

Rust is more important in soya R-stages, but in regions where disease pressure is high and condition favourable, the epidemic process can begin earlier, in soya V-stages. In this type of situation, a triazole is applied to hold down disease progress.

US application 2005/0223424 describes a method for treating soybean rust in a soybean plant comprising, identifying a soybean plant as being infected with rust, and applying a composition having glyphosate, alone or in combination with a fungicide, to the soybean plant or portion thereof, whereby the composition results in the disease being controlled.

Applicants have now found that improved methods of controlling asian soybean rust is achieved when a glyphosate tolerant plant propagation material is treated with a pesticidal composition comprising one or more defined fungicides, and then thereafter applying another pesticidal composition comprising glyphosate to the resulting soybean plant, part of plant and/or the locus thereof. Thereby the yield of the crop is improved.

Accordingly, in a first aspect the present invention provides a method for controlling asian soybean rust comprising (a) applying a pesticidal composition (A) to a glyphosate tolerant soybean plant propagation material, and (β) applying a pesticidal composition (B) to the resulting soybean plant, part of plant and/or the locus thereof one or more times (i) before emergence, (ii) after emergence, or (iii) both (i) and (ii), provided that composition (A) comprises one or more of flutriafol, triticonazole, tebuconazole, ipconazole, epoxyconazole, orysastrobin, prothioconazole, fluoxastrobin, azoxystrobin, furametpyr, cyproconazole, a compound of formula (I) and a compound of formula (B), and pesticide composition (B) comprises glyphosate; wherein compound (I) is represented by (I)

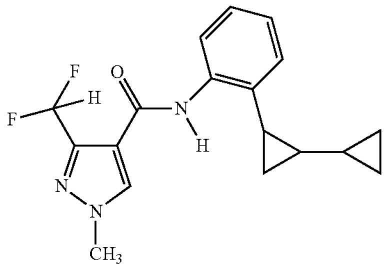

or a tautomer of such a compound, and compound (B) is represented by formula (B)

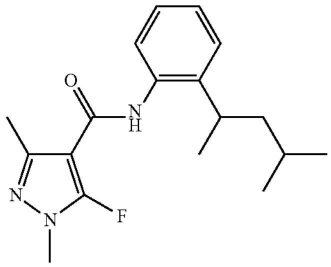

or a tautomer of such a compound.

In an embodiment of each aspect, an effective amount of composition (A) and composition (B) is applied. In particular, a synergistic amount of composition (A) and composition (B) is applied.

In an alternative of the first aspect, composition (A) comprises fluquinconazole, provided that the application of composition (A) in method step (α) is such the amount of fluquinconazole applied to glyphosate tolerant soybean plant propagation material is less than 50 g/100 kg of seeds.

In a second aspect, the present invention provides a method for controlling asian soybean rust comprising applying a pesticidal composition comprising a compound of formula (I) or a tautomer thereof as defined in the first aspect to a glyphosate tolerant soybean plant propagation material.

In a further aspect, a glyphosate tolerant soybean plant propagation material treated with a compound of formula (I) as defined in the first aspect is also provided.

In an aspect the present invention provides a method comprising step (α) and step (β) as defined in the first aspect. In an embodiment of this aspect, carrying out steps (α) and (β) achieve control of asian soybean rust.

For the avoidance of any doubt, step (β) follows step (α) wherein there is a step of planting or sowing the treated plant propagation material between steps (α) and (β).

In an embodiment, in either or both of step (α) and step (β) one or more further active compounds (such as other pesticides and other useful compounds) other than those/that defined in the first aspect may also be applied simultaneously or in any desired sequence with the compositions defined in step (α) and step (β).

In an embodiment, either or both compositions (A) and (B) comprise one or more further active compounds other than those/that defined in the first aspect.

Accordingly, the pesticide spectrum of the composition can be broadened or enhanced. The spectrum, therefore, may extend to another disease control related to ASR or independent thereof, insect control, and/or nematode control.

In a further aspect, the present invention provide a method for controlling asian soybean rust comprising applying a pesticidal composition, which comprises one or more of tebuconazole, ipconazole, flutriafol, epoxyconazole, triticonazole, fluquinconazole, prothioconazole and cyproconazole and one or more plant growth regulators, such as a gibberellic acid, to a soybean plant propagation material; preferably applying to a glyphosate tolerant soybean plant propagation material.

Pesticidal composition (A) and pesticidal composition (B) are herein also referred to as a fungicide-containing composition and a glyphosate-containing composition respectively.

Controlling, preventing or protecting and its inflections, within the context of the present invention, mean reducing any undesired effect, such as pathogenic, such as phytopathogenic, especially fungi, infestation or attack of, and pathogenic damage or pest damage on, a plant, part of the plant or plant propagation material to such a level that an improvement is demonstrated over a like plant, part of the plant or plant propagation material without treatment by the composition or method of the present invention.

The combination of steps comprising (α) and (β) as defined in the first aspect has very advantageous properties for protecting plants, in particular soybean plants, against (i) pathogenic, such as phytopathogenic, especially fungi, attack or infestation, especially ASR, which result in disease and damage to the plant, and/or (ii) pest attack or damage.

These properties are for example the synergistically enhanced actions of the compositions (A) and (B) as defined in the first aspect, resulting in lower pathogenic damage and/or pest damage, lower rates of application, or a longer duration of action.

Each of flutriafol, fluquinconazole, triticonazole, tebuconazole, ipconazole, epoxyconazole, orysastrobin, prothioconazole, fluoxastrobin, azoxystrobin, furametpyr, cyproconazole and a compound of formula (I) when applied as a treatment on to the plant propagation material of a soybean plant, followed by glyphosate application on the plants or part of plant and/or locus thereof demonstrates unexpectedly good ASR control on soybean plants. In particular, step (α) and step (β) as defined in the first aspect control ASR in early vegetative stage of the crop, i.e., up to V6.

Further, the application of the glyphosate also controls undesired vegetation in soybean plant fields without causing any appreciable damage to the plant. Undesired vegetation are those plants that affect the growth and quality of the useful soybean plants and examples include grasses and weeds.

Consequently, the present invention also provides a method for improving the growing characteristics of a soybean plant, which comprises the steps (α) and (β) as defined in the first aspect.

The improvement in the growing (or growth) characteristics of a plant can manifest in a number of different ways, but ultimately it results in a better product of the plant. It can, for example, manifest in improving the yield and/or vigour of the plant or quality of the harvested product from the plant, which improvement may or may not be connected to the control of diseases and/or pests.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed, for example, in terms of an amount by weight or volume of a product of the plant on some basis. The basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less water or fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that the present method is capable of "improving the yield and/or vigour" of a plant, the present method results in an increase in either the yield, as described above, or the vigor of the plant, as described above, or both the yield and the vigor of the plant.

By "glyphosate tolerant" is meant that the plants for use in the methods are resistant to glyphosate application or tolerant of glyphosate. Glyphosate tolerant plants are made tolerant to glyphosate by conventional breeding or having a transgenic event that provides glyphosate resistance. Some examples of such preferred transgenic plants having transgenic events that confer glyphosate resistance are described in U.S. Pat. Nos. 5,914,451; 5,866,775; 5,804,425; 5,776,760; 5,633,435; 5,627,061; 5,463,175; 5,312,910; 5,310,667; 5,188,642;

5,145,783; 4,971,908 and 4,940,835. The use of "stacked" transgenic events in the plant is also contemplated.

Stacked transgenic events including additional herbicide-resistant traits such as resistance to HPPD-inhibitors, sulfonyl-ureas, glufosinate and bromoxynil are widely used and described in readily available resources. The stacked transgenic events may also be directed to other pesticide resistant traits, such as insecticide, nematicide, fungicide, etc resistance, which may be made by conventional breeding or introducing a transgenic event.

Lines of transgenic glyphosate tolerant crop plants contemplated for use in the methods of the present invention include soybean, and other leguminous plants, for example, and Roundup Ready® Soybean 40-3-2. Production of transgenic lines of other plant species expressing a glyphosate-tolerance gene may be produced by techniques known in the art.

A "transgenic plant" refers to a plant that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of the polypeptide. The expression cassette can be introduced into a plant by transformation or by breeding after transformation of a parent plant. As previously described a plant refers to a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

An example of a glyphosate tolerant soybean event is MON89788 (also referred to as MON19788 or GM A19788). The soybean transgenic event designated MON89788 and progeny thereof having representative seed is deposited with American Type Culture Collection (ATCC) with accession No. PTA-6708.

The pesticides, such as the defined fungicides and herbicide in the first aspect, having a common name are described in the e-Pesticide Manual, version 3.0, 13th Edition, Ed. CDC Tomlin, British Crop Protection Council, 2003-04, along with their characteristics.

The compounds of formula (I) occur in different stereoisomeric forms, which are described in formulae $I_I$, $I_{II}$, $I_{III}$ and $I_{IV}$:

$I_I$

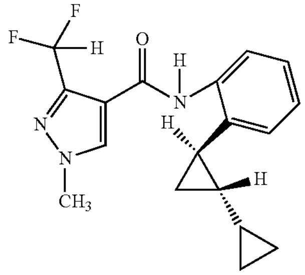

-continued $I_{II}$

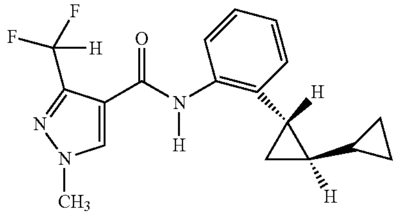

$I_{III}$

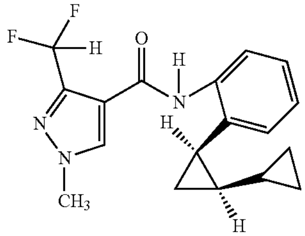

$I_{IV}$

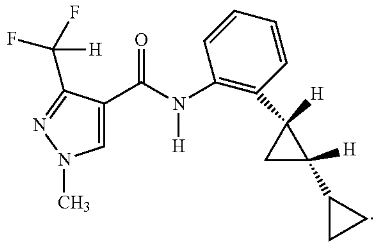

The invention covers all such stereoisomers and mixtures thereof in any ratio.

A preferred embodiment of the compound of formula (I) is a compound of the formula Ia (trans)

(Ia)

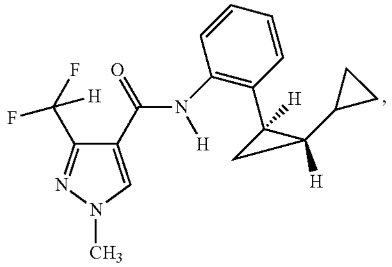

which represents a compound of formula $I_I$; a compound of formula $I_{II}$ or a mixture in any ratio of a compound of formula $I_I$ and a compound of formula $I_{II}$. Preferably, compound of formula (I) exists as a racemic compound of the formula Ia (trans), which represents a racemic mixture of a compound of formula $I_I$ and a compound of formula $I_{II}$.

A further preferred embodiment of the compound of formula (I) is a compound of the formula Ib (cis)

(Ib)

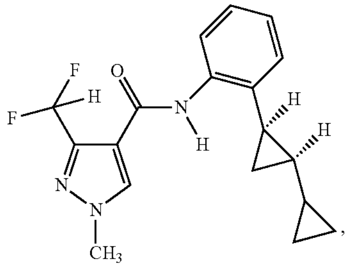

which represents a compound of formula $I_{III}$; a compound of formula $I_{IV}$ or a mixture in any ratio of a compound of formula $I_{III}$ and a compound of formula $I_{IV}$. compound (I) exists as a racemic compound of the formula Ib (cis), which represents a racemic mixture of a compound of formula $I_{III}$ and a compound of formula $I_{IV}$.

A further preferred embodiment of the compound of formula (I) exists as a racemic compound of formula I, wherein the ratio of racemic compounds of formula Ia, which represent a racemic mixture of compounds of formula $I_I$ and compounds of formula $I_{II}$, to racemic compounds of formula Ib, which represent a racemic mixture of compounds of formula $I_{III}$ and compounds of formula $I_{IV}$, is from 1:1 to 100:1.

Within said embodiment suitable ratios of racemic compounds of formula Ia, which represent a racemic mixture of compounds of formula $I_I$ and compounds of formula $I_{II}$ to racemic compounds of formula Ib, which represent a racemic mixture of compounds of formula $I_{III}$ and compounds of formula $I_{IV}$, are ratios such as 1:1, 2:1, 3:1, 4:1, 5:1, 6:1, 7:1, 8:1, 9:1, 10:1, 20:1, 50:1 or 100:1. Preference is given to ratios from 2:1 to 100:1, more preferably 4:1 to 10:1.

In a preferred embodiment compound of formula (I) exists as from 65, preferably 85, to 99% by weight of racemic compounds of formula Ia, which represent a racemic mixture of compounds of formula $I_I$ and compounds of formula $I_{II}$.

According to the instant invention, a "racemic mixture" of two enantiomers or a "racemic compound" means a mixture of two enantiomers in a ratio of substantially 50:50 of the two enantiomers.

The compounds of formula I and their manufacturing processes starting from known and commercially available compounds are described in WO 03/074491, WO 2006/015865 and WO 2006/015866.

The compounds of formula B are described in WO 03/010149 and WO 05/58839.

In an embodiment, composition (A) comprises compound (I) and one or more of fludioxonil, difenoconazole, mefenoxam, cyprodinil, thiabendazole and thiamethoxam.

Specific examples include compound (I), fludioxonil and, cyprodinil; compound (I), fludioxonil, and difenoconazole; compound (I), fludioxonil, difenoconazole and thiamethoxam; compound (I), difenoconazole and mefenoxam; compound (I), difenoconazole, mefenoxam and thiamethoxam; and compound (I), thiabendazole, mefenoxam and optionally fludioxonil. The ratio between any two compounds is preferably in the range of 1:4 to 4:1, in particular 1:2 to 2:1.

The compositions (A) and (B) are used in effective amounts. In respect of composition (B), the term "effective amount" means an amount of the glyphosate compound sufficient to result in any observable measure of ASR control, prevention or treatment in a plant. Preferably, an effective amount of glyphosate results in a concentration of glyphosate in a plant tissue of between about 0.01 parts per million (ppm) to about 100 ppm per fresh weight. More preferable, tissue concentrations of between 0.1 ppm and 25 ppm glyphosate of fresh weight are obtained in the tissues of plants treated in the methods of the present invention. Most preferably, tissue concentrations of between about 0.5 ppm and about 10 ppm glyphosate are effective in controlling, preventing or treating disease, especially ASR, in a fungicide treated soybean plant.

Effective rates of application in the present invention for a glyphosate compound can be influenced by many factors including the environment and should be determined under actual use conditions. Preferably, a rate of application of a glyphosate compound from about 0.1 pounds acid equivalent/acre (lb ae/acre, herein referred to lb/acre) to about 5 lb/acre of glyphosate is effective in controlling, preventing or treating a pathogen, such as ASR, in accordance with the method of the present invention. Yet more preferable are rates of application ranging from about 0.37 lb/acre (414 g ae/ha) to about 3.0 lb/acre (3360 g ae/ha), such as 0.37 lb/acre (414 g ae/ha) to about 2.5 lb/acre (2800 g ae/ha). Most preferable are rates of application of about from 0.75 lb/acre (840 g ae/ha) to 1.5 lb/acre (1680 g ae/ha).

Generally, glyphosate-containing composition can be applied, if applied only once, at a rate of 960 g ae/ha; if applied twice the rate can vary from 1200 to 1680 g ae/ha. The rates and number of applications vary according to the particular conditions. Preferably, the composition (B) is applied three times with an application rate of 960, 720 and 400 g ae/ha respectively.

In an embodiment, the present invention controls, prevents or treats *Phakopsora pachyrhizi* and/or *P. meibomiae*, especially *Phakopsora pachyrhizi*.

The present invention also provides methods for controlling undesired vegetation, such as harmful weeds, and controlling, preventing or treating ASR in a field of glyphosate tolerant soybean plants where the method uses applications of glyphosate compositions, such as glyphosate-containing composition (B). Such methods comprise one or more applications of a glyphosate composition to a field of glyphosate tolerant soybean plants, preferably two or more applications.

Preferably, the application or applications are timed for effective weed control and effective ASR control, prevention or treatment in the treated soybean plant.

For example, without limitation, a first application of glyphosate-containing composition (B) is applied at a time when the application controls the weeds within the field. For example, without limitation, a second application is at a time when the glyphospate tolerant soybean plants are either at risk of infection or have already been infected by ASR. A third application can also be envisaged to further prevent infection.

In an embodiment, methods for controlling undesired vegetation, such as weeds, and preventing, treating or controlling ASR in a field of glyphosate tolerant soybean plants comprises the steps of (a) treating a plant propagation material of a glyphosate tolerant soybean plant with a fungicide-containing composition (A), (b) planting or sowing the treated plant propagation material in a field, (c) substantially freeing the field of non-crop plants by applying a herbicidal composition and (d) thereafter apply a glyphosate-containing composition (B). In such a method, it should be appreciated that the steps of planting and substantially freeing can be interchanged. Thus, the field may be substantially free of non-crop plants before planting the treated glyphosate tolerant plant propagation material in the field. In one embodiment, the application of the herbicidal composition and the application of composition (B) are 1 day apart, 2, 3, 4, 5, 6, 7, 8, 9, 10, 14, 21 days apart. In another embodiment, the herbicidal and glyphosate-containing composition (B) applications are greater than 5, 10, 20, 25, 30, 35, 40, 45, or 50 days apart. In a further embodiment, the herbicidal composition and glyphosate-containing composition (B) are the same compositions (containing exactly the same components), and so the glyphosate-containing composition (B) is used in steps (c) and (d), preferably with a delay in applications as indicated above.

Generally, composition B is applied around 20 days after emergence and can also in addition be applied 30 days after emergence. Preferably, a third application about 40-45 days is also envisaged for rust control.

In one embodiment, the composition (B) is applied one or more times during the growing season. In another embodiment, the composition (B) is applied 2, 3, 4, 5, 6, 7, 8, 9, 10 times during the growing season to a glyphosate tolerant plant.

In respect of pesticidal composition (A), the term "effective amount" means an amount of the defined fungicide compound sufficient to provide early ASR control. Generally the rates depend on a number of conditions, such as plant propagation type, soil type, likely ASR pressure, and climatic conditions.

Generally, application rates of each of the defined fungicides can vary from 0.5 to 1000 g/100 kg of seeds of active ingredients.

Specific examples of application rates of the defined fungicides are

| | Al g/100 kg of seeds | | | |
|---|---|---|---|---|
| Flutriafol | 1-85 | 3-65 | 5-45 | 10-30 |
| Fluquinconazole | 15-49 | 15-45 | 15-40 | 20-30 |
| Triticonazole | 1-200 | 5-150 | 10-120 | 20-100 |
| Ipconazole | 1-150 | 5-100 | 5-80 | 10-60 |
| orysastrobin | 1-200 | 5-150 | 10-120 | 20-100 |
| azoxystrobin | 1-85 | 3-65 | 5-45 | 10-30 |
| fluoxastrobin | 1-200 | 5-150 | 10-120 | 20-100 |
| prothioconazole | 1-200 | 5-150 | 10-120 | 20-100 |
| epoxyconazole | 1-150 | 5-100 | 5-80 | 10-60 |
| tebuconazole | 1-85 | 3-65 | 5-45 | 10-30 |
| cyproconazole | 0.5-30 | 1-10 | 1.5-10 | 2-6 |
| furametpyr | 1-200 | 5-150 | 10-120 | 20-100 |
| a compound of formula (I) | 1-220 | 5-150 | 15-100 | 20-80 |
| a compound of formula (B) | 1-220 | 5-150 | 15-100 | 20-80 |

Whereas the fungicide-containing composition (A) is applied to a plant propagation material before ASR infection, the glyphosate-containing composition (B) can be applied either pre- or post-ASR infection, or both pre- and post-infection. In an embodiment, a glyphosate is translocated through the vascular system in plants and therefore the entire plant is not required to be contacted with glyphospate-containing composition (B). In an embodiment, a glyphosate-containing composition (B) is applied pre-ASR infection.

Gylphosate, as used herein, refers to N-phosphonomethylglycine and the salts thereof. Glyphosate is typically used in form of its monobasic, dibasic or tribasic salts. Dibasic salts, such as the diammonium salt, of glyphosate are useful in compositions of the invention, but monobasic salts are generally preferred. Of these, particularly preferred examples include the monosodium, monopotassium, monoammonium, mono(dimethylammonium), mono(ethanolammonium), mono(isopropylammonium) and mono(trimethylsulfonium) salts as well as mixtures thereof. Commercial products of glyphosate are of different glyphosate salts, different formulation types and concentrations. A preferred glyphosate formulation is a potassium salt of glyphosate with a tallowamine (5EO) ethoxylate surfactant.

The term "plant propagation material" is understood to denote all the generative parts of the plant, such as seeds, which can be used for the multiplication of the latter and vegetative plant material such as cuttings and tubers (for example, potatoes). There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion, for example, of their roots.

The term "plant" includes whole plants and the term "part of plant", includes, but not limited to, parts and organs above the ground, such as shoot vegetative organs/structures mainly above the ground.

The glyphosate-containing composition (B) is applied either directly on a soybean plant, or immediately adjacent to the plant (or to locus of the plant) where the glyphosate can be taken-up into the soybean plant's vascular system. The gylphosate-containing composition (B) is directly contacted with the soybean plant, the composition may be contacted with the entire plant or with only a portion of the plant. In a preferred aspect, the soybean plant is contacted with a glyphosate-containing composition (B) by overhead spraying of the composition. Application of glyphosate-containing composition (B) to foliage of plants is preferably accomplished by spraying, using any conventional means for spraying liquids, such as spray nozzles or spinning-disk atomizers. A glyphosate-containing composition (B) is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (1/ha), preferably about 50 to about 3001/ha, by spray application.

Methods for applying or treating pesticidal active ingredients and mixtures thereof on to plant propagation material, especially seeds, are known in the art, and include dressing, coating, pelleting and soaking application methods of the propagation material. In a preferred embodiment, the active ingredient(s) is (are) applied or treated on to the plant propagation material by a method such that the germination is not induced; generally seed soaking induces germination because the moisture content of the resulting seed is too high. Accordingly, examples of suitable methods for applying (or treating) a plant propagation material, such as a seed, are seed dressing, seed coating or seed pelleting and the like.

It is preferred that the plant propagation material is a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the active ingredients and adherence thereof to the seeds is desired during propagation material treatment. Treatment could vary from a thin film (dressing) of the formulation containing the active ingredient(s) on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the active ingredient(s). In particular, seed coating or seed pelleting are preferred in the treatment of the active ingredient(s) according to the invention. As a result of the treatment, the active ingredient(s) is (are) adhered on to the seed and therefore available for pathogenic and/or pest control.

The treated seeds can be stored, handled, sowed and tilled in the same manner as any other active ingredient treated seed.

The glyphosate-containing composition (B) may contain other pesticides, such as other herbicides, fungicides, insecticides, acaricides, nematicides. Alternatively, such other pesticides may be applied simultaneously with composition (B) to the plant, part of plant and/or or locus thereof or separately either before or after the glyphosate-containing composition (B) application.

Similarly, the fungicide-containing composition (A) may contain other pesticides, such as other fungicides, insecticides, acaricides, nematides. Alternatively, such other pesticides may be applied or treated simultaneously with composition (A) to the plant propagation material, or separately either before or after the fungicide-containing composition (A) application/treatment.

The glyphosate tolerant soybean plant propropation material may also be applied or treated together and/or sequentially with further useful compounds. These further useful compounds can be fertilizers or micronutrient donors (such as Mo, Zn and/or Co) or other preparations that influence plant growth, such as inoculants (e.g. a strain of nitrogen-fixing bacteria), plant inducers (e.g. nod factors—see US2005187107, which hereby incorporated). In an embodiment, the glyphosate tolerant soybean plant propagation material is treated with inoculants, such as *Rhizobium* spp, and/or plant inducers, e.g. a nod factor derived from *Bradyrhizobium japonicum, Sinorhizobium fredii, Sinorhizobium meliloti, Bradyrhizobium* sp. (*Arachis*), or *Rhizobium leguminosarum* biovar *phaseoli, viceae*, or *trifolii.*

A single pesticidal active ingredient may have activity in more than one area of pest control, for example, a pesticide may have fungicide, insecticide and nematicide activity. Specifically, aldicarb is known for insecticide, acaricide and nematicide activity, while metam is known for insecticide, herbicide, fungicide and nematicide activity, and thiabendazole and captan can provide nematicide and fungicide activity.

Examples of pesticides include herbicides, fungicides, bactericides, insecticides, acaricides and nematicides, for example, triazole derivatives, strobilurins, carbamate (including thiocarbamate), benzimidazoles (thiabendazole), N-trihalomethylthio compounds (captan), substituted benzenes, carboxamides, phenylamides and phenylpyrroles, and mixtures thereof; and neonicotinoids, avermectin and derivatives thereof, carbamates and pyrethroids.

In an embodiment, independent of the defined fungicide in composition (A), step ($\alpha$) comprises application to a plant propagation material one or more other pesticides selected from difenoconazole, benalaxyl, benalaxyl-M, cyprodinil, carboxin, trifloxystrobin, metalaxyl, metalaxyl-M (mefenoxam), tolyfluanid, dichlofluanid, fludioxonil, fenarimol, nuarimol, pyrifenox, triadimenol, benomyl, carbendazim, carboxin, flutolanil, fuberizadole, guazatine, ipconazole, iprodione, pencycuron, prochloraz, propamocarb, silthiofam, thiabendazole, thiram, triazoxide, a pesticidal active manganese compound (such as mancozeb, maneb), tefluthrin, thiodicarb, thiamethoxam, clothianidin, fipronil, lambda-cyhalothrin, chlorantraniliprole, flubendamide, imidacloprid and abamectin.

In an embodiment, pesticidal composition (A) further comprises, independent of the defined fungicide, one or more other pesticides selected from difenoconazole, benalaxyl, benalaxyl-M, cyprodinil, carboxin, trifloxystrobin, metalaxyl, metalaxyl-M (mefenoxam), tolyfluanid, dichlofluanid, fludioxonil, fenarimol, nuarimol, pyrifenox, triadimenol, benomyl, carbendazim, carboxin, flutolanil, fuberizadole, guazatine, ipconazole, iprodione, pencycuron, prochloraz, propamocarb, silthiofam, thiabendazole, thiram, triazoxide, a pesticidal active manganese compound (such as mancozeb, maneb), tefluthrin, thiodicarb, thiamethoxam, clothianidin, fipronil, lambda-cyhalothrin, chlorantraniliprole, flubendamide, imidacloprid and abamectin.

Preferred examples of plant growth regulators are gibberellic acid (gibberellin $A_3$), gibberellin $A_4$ and gibberellin $A_7$. The plant growth regulator is applied at an effective rate, and can be applied at a rate of 0.01 to 10, preferably 0.1 to 5, more preferably 0.7 to 3, such as 0.8 to 1.5 g/100 kg of seeds.

In an embodiment, tebuconazole and one or more gibberellic acid (gibberellin $A_3$), gibberellin $A_4$ and gibberellin $A_7$, are applied to a GLY tolerant soybean plant propagation material.

In an embodiment, ipconazole and one or more gibberellic acid (gibberellin $A_3$), gibberellin $A_4$ and gibberellin $A_7$, are applied to a GLY tolerant soybean plant propagation material.

In an embodiment, flutriafol and one or more gibberellic acid (gibberellin $A_3$), gibberellin $A_4$ and gibberellin $A_7$, are applied to a GLY tolerant soybean plant propagation material.

In an embodiment, epoxyconazole and one or more gibberellic acid (gibberellin $A_3$), gibberellin $A_4$ and gibberellin $A_7$, are applied to a GLY tolerant soybean plant propagation material.

In an embodiment, triticonazole and one or more gibberellic acid (gibberellin $A_3$), gibberellin $A_4$ and gibberellin $A_7$, are applied to a GLY tolerant soybean plant propagation material.

In an embodiment, fluquinconazole and one or more gibberellic acid (gibberellin $A_3$), gibberellin $A_4$ and gibberellin $A_7$, are applied to a GLY tolerant soybean plant propagation material.

In an embodiment, prothioconazole and one or more gibberellic acid (gibberellin $A_3$), gibberellin $A_4$ and gibberellin $A_7$, are applied to a GLY tolerant soybean plant propagation material.

In an embodiment, cyproconazole and one or more gibberellic acid (gibberellin $A_3$), gibberellin $A_4$ and gibberellin $A_7$, are applied to a GLY tolerant soybean plant propagation material.

In an embodiment, independent of the defined herbicide in composition (B), step ($\beta$) comprises application to the resulting soybean plant, part of plant and/or the locus thereof one or more other pesticides selected from S-metolachlor, metolachlor, chlorimuron-ethyl, atrazine, benoxacor, thiamethoxam, imidacloprid, abamectin, emamectin, clothianidin, diazinon, dichlobenil, dicamba, 2,4-D, fomesafen, fluazifop-P-butyl, paraquat, diquat, diuron, flazasulfuron, terbuthylazine, azoxystrobin, cyproconazole, fludioxonil, difenoconazole, cyproconazole, thiabendazole, acibenzolar-5-methyl, epoxiconazole, propiconazole, boscalid, penthiopyrad, chlorothalonil, mancozeb, flutriafol, fluquinconazole, triticonazole, ipconazole, orysastrobin, picoxystrobin, pyraclostrobin, cyprodinil, fenpropimorph, fenpropidin, tebuconazole, tetraconazole, prothioconazole, a compound of formula F-5, and a compound of formula F-10 to F-13.

The other pesticides may be applied to the resulting soybean plant, part of plant and/or the locus thereof one or more times (i) before emergence, (ii) after emergence, or (iii) both (i) and (ii).

In an embodiment, pesticidal composition (B), independent of use in composition (A), further comprises one or more other pesticides selected from S-metolachlor, metolachlor, chlorimuron-ethyl, atrazine, benoxacor, thiamethoxam, imidacloprid, abamectin, emamectin, clothianidin, diazinon, dichlobenil, dicamba, 2,4-D, fomesafen, fluazifop-P-butyl, paraquat, diquat, diuron, flazasulfuron, terbuthylazine, azoxystrobin, cyproconazole, fludioxonil, difenoconazole, cyproconazole, thiabendazole, acibenzolar-5-methyl, epoxiconazole, propiconazole, boscalid, penthiopyrad, chlorothalonil, mancozeb, flutriafol, fluquinconazole, triticonazole, ipconazole, orysastrobin, picoxystrobin, pyraclostrobin, cyprodinil, fenpropimorph, fenpropidin, tebuconazole, tetraconazole, prothioconazole, a compound of formula F-5, and a compound of formula F-10 to F-13.

Preferred fungicides for use in step (β) or in composition (B), independent of use in step (α) or in composition (A), are tebuconazole, epoxiconazole, mixture of epoxiconazole and pyraclostrobin, cyproconazole, mixture of cyproconazole and azoxystrobin, flutriafol and tetraconazole.

As an example, cyproconazole can be applied in step (β) at a rate of about 30 g/ha, and mixture of cyproconazole and azoxystrobin can be applied in step (β) at a rate of 24+60 g/ha as cyproconazole and azoxystrobin respectively.

Preferably, an application of a fungicide simultaneous with composition (B) or as part of composition (B) or in any desired sequence to composition (B) occurs 40-50 days after emergence and optionally also 14-21 days later.

Compound of formula F-5 is represented by (F-5)

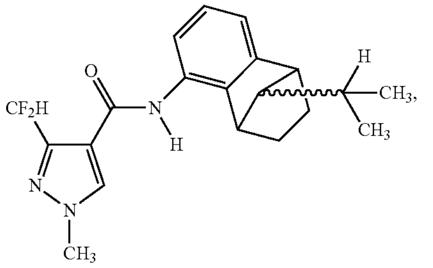

which represents an epimeric mixture of the racemic compounds of formula F-3 (syn) and F-4 (anti), wherein the ratio of racemic compounds of formula F-3 (syn) to racemic compounds of formula F-4 (anti) is from 1000:1 to 1:1000, wherein F-3 and F-4 are represented by (F-3)

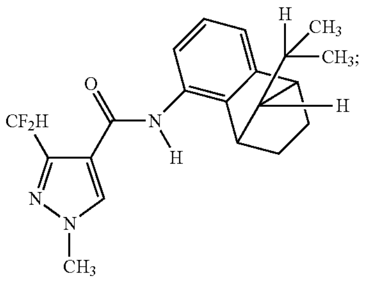

-continued (F-4)

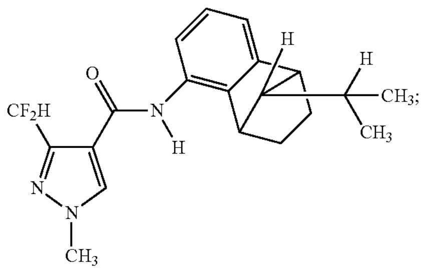

Compound of formula F-10 is represented by (F-10)

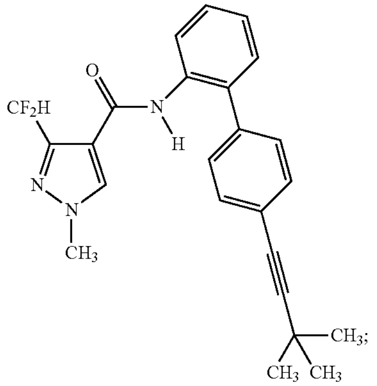

Compound of formula F-11 is represented by (F-11)

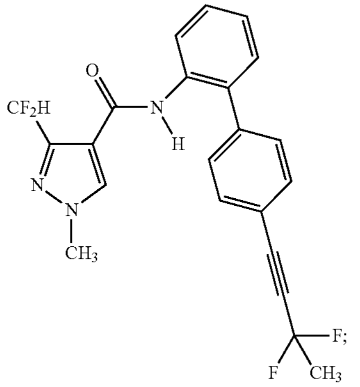

Compound of formula F-12 is represented by (F-12)

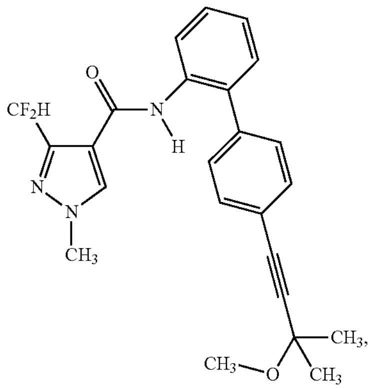

Compound of formula F-13 is represented by (F-13)

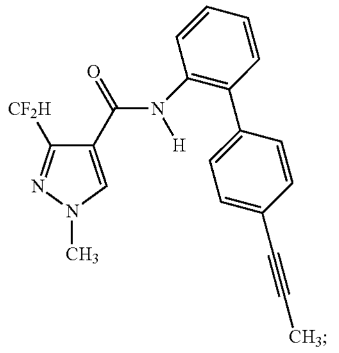

Generally the compositions (A) and (B) are formulated in a variety of ways using formulation adjuvants, such as carriers, solvents and surface-active substances for their specific application methods.

The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredients with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the mixture according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylne carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl-formamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifiying, wetting or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides and also liquid and solid fertilisers.

The mixture according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example, the methyl esters of lauric acid, palmitic acid and oleic acid, being important; those esters are known as methyl laurate (CAS-111-82-0), methyl palmitate (CAS-112-39-0) and methyl oleate (CAS-112-62-9) respectively. A preferred fatty acid methyl ester derivative is Emery® 2230 or 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pen-e-trate®, can also be mixed into the spray mixture as activity-enhancing agents.

The formulations are prepared in known manner, e.g., by homogeneously mixing and/or grinding the active ingredients with extenders, e.g., solvents, solid carriers and, where appropriate, surface-active compounds (surfactants).

Generally, a tank-mix formulation for foliar or soil application (e.g. glyphosate-containing composition (B)) comprises 0.1 to 20%, especially 0.1 to 15%, active ingredient compounds, and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Typically, a pre-mix formulation for foliar application (e.g. glyphosate-containing composition (B)) comprises 0.1 to 99.9%, especially 1 to 95%, active ingredient compounds, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application (e.g. fungicide-containing composition (A)) comprises 0.25 to 80%, especially 1 to 75%, active ingredient compounds, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application (e.g. fungicide-containing composition (A)) comprises 0.5 to 99.9%, especially 1 to 95%, active ingredient compounds, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

Preferred formulations for either composition (A) or (B) have especially the following compositions:

(%=percent by weight; "active ingredient mixture" denotes a mixture of compounds according to the compositions of the instant invention):

Emulsifiable Concentrates:

active ingredient(s): 1 to 95%, preferably 60 to 90% surface-active agent: 1 to 30%, preferably 5 to 20 liquid carrier: balance

Dusts:

active ingredient(s): 0.1 to 10%, preferably 0.1 to 5% solid carrier: 99.9 to 90%, preferably 99.9 to 99%

Suspension Concentrates:

active ingredient(s): 5 to 75%, preferably 10 to 50% surface-active agent: 1 to 40%, preferably 2 to 30% water: balance

Wettable Powders:

active ingredient(s): 0.5 to 90%, preferably 1 to 80% surface-active agent: 0.5 to 20%, preferably 1 to 15% solid carrier: balance

Granules:

active ingredient(s): 0.1 to 30%, preferably 0.5 to 15% solid carrier: 99.9 to 70%, preferably 99.5 to 85%

The following Examples further illustrate, but do not limit, the invention in respect formulation types for the compositions according to the invention:

| F1. Emulsifiable concentrates | a) | b) | c) | d) |
|---|---|---|---|---|
| active ingredient(s) | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient(s) | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient(s) | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient(s) | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient(s) | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient(s) | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient(s) | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient(s) | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

Using such formulations either straight or diluted plant propagation material, plants, part of plant, or locus thereof can be treated and protected against damage, for example, from pests and/or pathogen(s), by, for example, spraying, pouring, coating or immersing.

The formulations of the present invention are distinguished by the fact that they are especially well tolerated by plants and are environmentally friendly.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

Use of a term in a singular form also encompasses that term in plural form and use of a term in the plural form also encompasses that term in the singular.

The following Examples are given by way of illustration and not by way of limitation of the invention.

BIOLOGICAL EXAMPLES

Example 1

Evaluation of Crop Tolerance and Activity Against *Phakopsora pachyrhizi*

Fifty soybean seeds of cv. S-40-R9 (RR-soybean) or cv. Williams (not GM) are sown 2 cm deep into trays filled with quarz sand. Seeds are treated prior to sowing with the formulated ais. The plants are grown at 20-23° C. in a greenhouse. If necessary, artificial lighting is supplied to give a 14 hr day.

Crop Tolerance Test

Plant emergence 6 DAS and final stand 11 DAS is counted.

Test for Rust Activity

For the soybean rust assay, plants are transplanted 13 DAS into 8 cm pots filled with soil. 13 days after transplanting leaf discs are cut from the first and second true leaves and transferred to multiwell plates filled with water agar. 1 day later the leaf discs are inoculated with *Phakopsora pachyrhizi*. Assessment of the disease incidence is done 11 DAI (days after inoculation).

Cyproconazole solo treatments caused severe reductions in plant numbers and size, which made it impossible to obtain leaf discs for soybean rust testings.

The results are illustrated in Tables 1 and 2.

TABLE 1

Influence of seed treatments with GA, CCZ, CCZ + GA on germination of soybean cv. S-40-R9 and activity against *P. pachyrhizi*

| | | | Germination | | | | 1st Leaf | | 2nd Leaf | |
|---|---|---|---|---|---|---|---|---|---|---|
| Nr. | | rate in g ai/100 kg | Count 6 DAS | % Emergence 6 DAS | Count 11 DAS | % Final Stand 11 DAS | % Disease | % Activity | % Disease | % Activity |
| 1 | Check untreated | 0 | 47 | 94 | 47 | 94 | 80.8 | 0 | 67.4 | 0 |
| 2 | Gibberelic acid (GA) | 1 | 50 | 100 | 50 | 100 | 87.8 | 0.0 | 71.1 | 0.0 |
| 3 | Gibberelic acid (GA) | 2 | 48 | 96 | 48 | 96 | 82.8 | 0.0 | 68.9 | 0.0 |
| 4 | Cyproconazole (CCZ) | 5 | 0 | 0 | 7 | 14 | NT | NT | NT | NT |
| 2 + 4 | CCZ + GA | 5 + 1 | 19 | 38 | 42 | 84 | 0 | 100.0 | 0 | 100.0 |
| 3 + 4 | CCZ + GA | 5 + 2 | 14 | 28 | 37 | 74 | 0 | 100.0 | 0 | 100.0 |
| 5 | Cyproconazole (CCZ) | 10 | 0 | 0 | 17 | 34 | NT | NT | NT | NT |
| 2 + 5 | CCZ + GA | 10 + 1 | 15 | 30 | 38 | 76 | 0 | 100.0 | 0 | 100.0 |
| 3 + 5 | CCZ + GA | 10 + 2 | 30 | 60 | 47 | 94 | 0 | 100.0 | 0 | 100.0 |

NT = No test possible due to phytotoxicity on and stunting of the soybean plants, DAS = Days after sowing

TABLE 2

Influence of seed treatments with GA, CCZ, CCZ + GA on germination of soybean cv. Williams and activity against *P. pachyrhizi*

| | | | Germination | | | | 1st Leaf | | 2nd Leaf | |
|---|---|---|---|---|---|---|---|---|---|---|
| Nr. | | rate in g ai/100 kg | Count 6 DAS | % Emergence 6 DAS | Count 11 DAS | % Final Stand 11 DAS | % Disease | % Activity | % Disease | % Activity |
| 1 | Check untreated | 0 | 48 | 96 | 48 | 96 | 77.7 | 0 | 71.4 | 0 |
| 2 | Gibberelic acid (GA) | 1 | 50 | 100 | 50 | 100 | 88.9 | 0.0 | 48.3 | 32.4 |
| 3 | Gibberelic acid (GA) | 2 | 49 | 98 | 49 | 98 | 87.2 | 0.0 | 51.1 | 28.4 |
| 4 | Cyproconazole (CCZ) | 5 | 0 | 0 | 27 | 54 | NT | NT | NT | NT |
| 2 + 4 | CCZ + GA | 5 + 1 | 43 | 86 | 49 | 98 | 0 | 100.0 | 0 | 100.0 |
| 3 + 4 | CCZ + GA | 5 + 2 | 42 | 84 | 49 | 98 | 0 | 100.0 | 0 | 100.0 |
| 5 | Cyproconazole (CCZ) | 10 | 0 | 0 | 38 | 76 | NT | NT | NT | NT |
| 2 + 5 | CCZ + GA | 10 + 1 | 38 | 76 | 47 | 94 | 0 | 100.0 | 0 | 100.0 |
| 3 + 5 | CCZ + GA | 10 + 2 | 43 | 86 | 48 | 96 | 0 | 100.0 | 0 | 100.0 |

NT = No test possible due to phytotoxicity on and stunting of the soybean plants, DAS = Days after sowing

Example 2

Details of the fungicide and glyphosate applications to glyphosate tolerant soya seeds are provided in Table 3. The seeds are then planted in randomised plot sizes of 3×5 meters (4 replicates).

The yield of the resulting crop is illustrated in Table 4.

TABLE 3

| treatment & application details | | | | | | |
|---|---|---|---|---|---|---|
| | | | Glyphosate foliar spray | | | |
| | Seed Treatment | | V2/v3 | | V2/V3 + 14 days | |
| treat-ment | active ingredient | g AI/100 Kg | product | g AI/100 Kg | product | g AI/100 Kg |
| 1 | — | — | — | — | — | — |
| 2 | — | — | GLY 1 | 720 | GLY 1 | 480 |
| 3 | | | GLY 2 | 720 | GLY 2 | 480 |
| 4 | Com-pound (1) | 40 | — | — | — | — |
| 5 | Com-pound (1) | 40 | GLY 1 | 720 | GLY 1 | 480 |
| 6 | Com-pound (1) | 40 | GLY 2 | 720 | GLY 2 | 480 |
| 7 | Com-pound (1) | 80 | GLY 2 | 720 | GLY 2 | 480 |

GLY 1 is a commercial glyphostae formulation available from a Syngenta Company.
GLY 2 is a commercial glyphostae formulation available from a Monsanto Company.

TABLE 4

| Yield data (from 2 trials) | | | | |
|---|---|---|---|---|
| | Yield kg/ha | | | |
| treatment | min | max | med | difference from check |
| 1 | 2134 | 2990 | 2562 | 0 |
| 2 | 2110 | 3171 | 2641 | 79 |
| 3 | 2081 | 3250 | 2665 | 103 |
| 4 | 2051 | 3092 | 2571 | 9 |
| 5 | 2450 | 3122 | 2786 | 224 |

TABLE 4-continued

| Yield data (from 2 trials) | | | | |
|---|---|---|---|---|
| | Yield kg/ha | | | |
| treatment | min | max | med | difference from check |
| 6 | 2765 | 3372 | 3068 | 506 |
| 7 | 2959 | 3032 | 2996 | 434 |

The invention claimed is:

1. A method for improving the yield of a soybean plant comprising:

(α) applying a pesticidal composition (A) comprising a compound of formula (I)

(I)

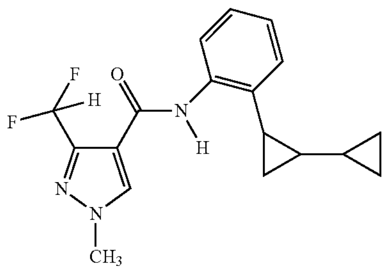

or a tautomer of such a compound, to a glyphosate tolerant soybean plant propagation material, and (β) applying a pesticidal composition (B) comprising glyphosate to the resulting soybean plant, part of plant and/or the locus thereof one or more times (i) before emergence, (ii) after emergence, or (iii) both (i) and (ii).

2. The method according to claim 1, wherein the propagation material is a seed.

3. The method according to claim 1, wherein the composition (B) is applied after emergence.

4. The method according to claim 1, wherein the glyphosate tolerant soybean plant is a MON89788 soybean.

* * * * *